United States Patent [19]

Sogi et al.

[11] 4,231,403
[45] Nov. 4, 1980

[54] LIQUID FEEDER FOR AUTOMATIC CULTURE APPARATUS

[75] Inventors: Shinroku Sogi; Makoto Yoshinaga, both of Hachioji; Toshio Shinohara, Chofu; Takayuki Aihara; Ikuo Tawara, both of Hachioji, all of Japan

[73] Assignee: Olympus Optical Co., Ltd., Tokyo, Japan

[21] Appl. No.: 973,116

[22] Filed: Dec. 26, 1978

Related U.S. Application Data

[62] Division of Ser. No. 876,894, Feb. 13, 1978, Pat. No. 4,179,339.

[30] Foreign Application Priority Data

Mar. 2, 1977 [JP] Japan .................................. 52-24766
Apr. 5, 1977 [JP] Japan .................................. 52-41589
Apr. 5, 1977 [JP] Japan .................................. 52-41592

[51] Int. Cl.³ ............................................. B65B 3/04
[52] U.S. Cl. .................................... 141/284; 141/87; 435/287; 435/289
[58] Field of Search ................... 141/284, 248, 86, 87, 141/88; 435/287, 289, 30, 33, 291; 422/63, 100; 195/127, 103.5 R

[56] References Cited

U.S. PATENT DOCUMENTS

| 2,654,522 | 10/1953 | Gorham | 141/86 |
| 3,124,173 | 3/1964 | Tiffany | 141/284 |
| 3,728,227 | 4/1973 | Elson et al. | 141/284 |
| 3,772,154 | 11/1973 | Isenberg et al. | 435/33 |

Primary Examiner—Houston S. Bell, Jr.
Attorney, Agent, or Firm—Ostrolenk, Faber, Gerb & Soffen

[57] ABSTRACT

A liquid feeder comprises a motor which drives a cam causing a vertical motion of a drive shaft which is also angularly driven by a cam groove, the drive shaft being effective to cause a three dimensional motion of the discharge port of a single liquid supply tube for injection into a pair of vessels.

3 Claims, 4 Drawing Figures

LIQUID FEEDER FOR AUTOMATIC CULTURE APPARATUS

RELATED APPLICATIONS

This is a divisional of U.S. patent application Ser. No. 876,894, filed Feb. 13, 1978, now U.S. Pat. No. 4,179,339.

BACKGROUND OF THE INVENTION

The present invention relates to a liquid feeder for automatic culture apparatus, and more particularly to a liquid feeder for injection of a liquid such as a culture, buffer or enzyme solution into a culture vessel in an automatic culture apparatus in which biological tissues or cells are automatically cultured.

The technique of culturing biological tissues and cells represents as essential fundamental experimental process in various fields including the medical, biological, pharmaceutical and agricultural fields. However, the culture of biological tissues and cells over successive generations involve a technical difficulty, which prevents a stable strain being cultured from being obtained in practice. Thus, there has been a need for a procedure for culturing biological tissues and cells which enable a stabilized strain being cultured to be obtained. Recently, a culture technique in a gaseous environment within an incubator has been developed, and has enabled the culturing over successive generations of cells of a particular variety such as those of liver, neuron, pituitary gland which have been considered difficult to be cultured.

The culture over successive generations will be briefly summarized below. A given number of cells is diluted in a culture solution in the form of a suspension, which is injected into a culture vessel such as petri dish. The vessel is placed in an incubator which cultures the cells under a given gas atmosphere. After a predetermined period of time, the vessel is removed from the incubator and the number of growth of cells are counted under a microscope. When it is determined that the intended cells have grown over the full extent of the vessel, it is transferred to a strain-free clean bench and the culture solution in the vessel is withdrawn with a pipette and disposed. Subsequently, a buffer solution is injected into the vessel to clean the remaining cells, and then withdrawn for disposal with a pipette. The grown cells which attach to the bottom of the vessel are rendered freely removable therefrom by the injection of an enzyme solution such as trypsin and allowing the vessel to remain intact for a given period. After the predetermined period, the enzyme solution is withdrawn from the vessel with a pipette and disposed, and a culture solution is again injected into the vessel. The culture solution is repeatedly withdrawn and discharged through the pipette to cause an oscillation or agitation which enables the grown cells to be completely released from the bottom of the vessel and suspended in the culture solution. The cells in suspension are transferred into a centrifuge tube with a pipette, and placed in a centrifuge the cells from the solution. Thereupon the cells attach to the bottom of the tube while the culture solution will be a decantered solution, which is disposed by tilting the tube. A culture solution is again injected into the centrifuge tube and is agitated by utilizing the withdrawing and discharging operation through the pipette to separate the cells from each other so that they are uniformly suspended in the culture solution within the centrifuge tube. Finally, the solution is distributed into a pair of culture vessels in an equal amount to complete one culture operation.

It will be recognized by those skilled in the art that the foregoing culture technique makes it necessary to remove the culture vessel out of the incubator and to expose it to the outer atmosphere in order to examine the growth of the tissues or cells under a microscope. This causes a sudden change in the culture conditions since the cells or tissues are placed out of a given environment maintained within the incubator including a gas atmosphere, temperature and humidity. This causes a delicate influence upon the tissues or cells being cultured and also involves an unavoidable contamination thereof by miscellaneous strains present in the atmosphere.

In addition, the various operations required for culturing over successive generations which should take place based on the results of observation with the microscope rely on a manual operation by an operator in the clean bench. This means that any slight difference in the various operations from operator to operator may have a direct influence upon the culturing result of the tissues or cells. Since the experience and skill of culturing technique varies from operator to operator, it is difficult to provide a standard procedure for the culturing technique, and this makes it impossible to obtain cultured tissues or cells of uniform quality. As a consequence, for different groups of researchers conducting a common study on the same theme, the conclusions reached may depend on the quality of the tissues being cultured. In extreme cases, the conclusions may be opposite to each other. Thus it will be seen that the reliability cannot be expected when the tissues or cells are cultured with the conventional technique.

It is generally accepted that it takes at least two years to train a skilled operator. As a result, there exists, a continued demand for skilled operators. As a consequence, researchers often have to perform the culturing operation themselves rather than devotedly directing their efforts to their study.

In view of these considerations, the present invention is directed to an automatic culture apparatus capable of automatically performing the above described culturing operation. As a result, the present invention eliminates the contamination which may occur as a result of the exposure to the atmosphere, eliminates the influence of manual operations upon the cultured results and permits a standard and uniform procedure for the various culturing operations to be established.

An automatic culture apparatus meeting the above requirements must be provided with a liquid supply system or liquid feeder which supplies various liquids or solutions such as buffer, enzyme and culture solutions to the culture vessel or centrifuge tube. The liquid supply system must include a refrigerator for storing the buffer, enzyme or culture solution. This refrigerator cannot, however, be housed within an incubator having a limited capacity since a large quantity of such solutions is required. As a result, it is necessary to provide a liquid supply from outside the incubator to a given location within the incubator maintained under a predetermined environment. In addition, the entire liquid feeder must be sterilized before it is assembled with the automatic culture apparatus. If the feeder is disassembled before sterilization, the parts may be subjected to contamination by strains during the assembly which follows the sterilization step, adversely influencing the subsequent culturing operation. It is desirable, therefore, to design the feeder so that it can be sterilized without requiring the disassembly thereof. It is also desirable that the liquid feeder be designed such that it can be mounted to extend into the incubator so that it is easily detachable in order to permit its replacement by a fresh feeder whenever the stored solution or solutions are exhausted. In addition, a leakage of the atmosphere through the connection must be prevented.

After a buffer solution is injected into the vessel of the automatic culture apparatus, it becomes necessary to switch the supply from a buffer solution to an enzyme solution since it is desired to inject the enzyme solution into the same vessel. The conventional practice is to inject two different solutions selectively into the same vessel. This has been done utilizing a pair of separate injection pumps which are connected with supply tube of the respective solutions. The tubes have their discharge port located above the vessel, and the pumps are separately operated. However, the location of the discharge port of the respective supply tubes above the vessel was undesirable since residual solution sometimes dripped down from the port after the injection of the solution ceased resulting in a possible contamination of the vessel. Accordingly, the prior art technique was inadequate for a culturing procedure for which a high accuracy is required.

During the culturing operation, it is also required for the liquid feeder to provide a three dimensional movement of a single discharge port in order to inject the culture solution into a culture vessel and a centrifuge tube which are located at different sites. The conventional practice has been to use a pair of motors, one for vertical movement and the other for rotation. In order to control the termination or stop position of the vertical and rotational movements, there must be provided four limit switches in total, which resulted in a complex arrangement, which is also liable to malfunctioning by the failure of the limit switches.

SUMMARY OF THE INVENTION

It is the object of the invention to provide a liquid feeder for automatic culture apparatus which supplies a single liquid to a pair of vessels which assume different three dimensional positions, by utilizing a simple arrangement, incorporating a pair of limit switches and a single motor to achieve a three dimensional movement of a liquid discharge port.

The three dimensional switching system of the invention achieves a three dimensional movement of the discharge port with a single motor and a pair of microswitches rather than a pair of motors and four limit switches as has been conventional, thus simplifying the arrangement. The failure is also reduced, assuring a reliable operation of the system.

DESCRIPTION OF PREFERRED EMBODIMENT

Figure 1:
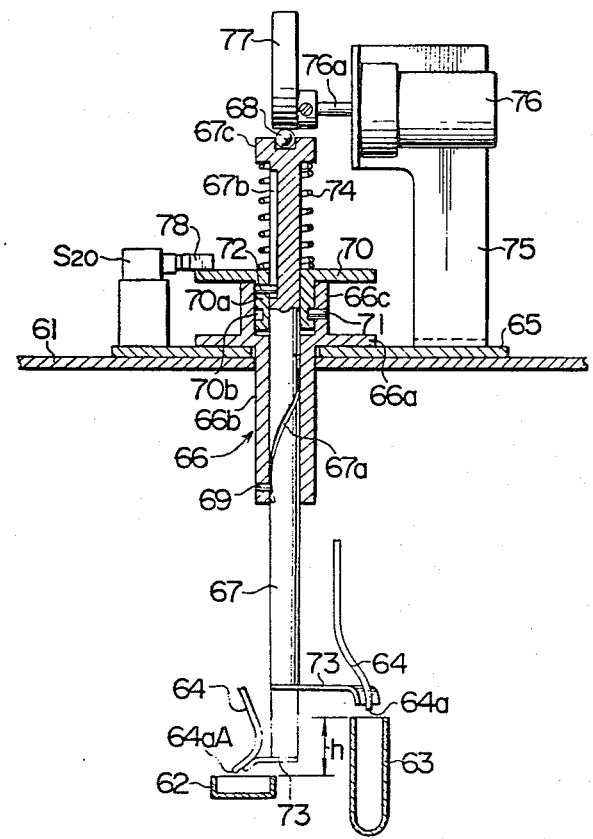
FIG. 1 is a side elevation, partly in section, of a three dimensional liquid supply switching system according to a further embodiment of the invention.

FIG. 1 shows a three dimensional supply switching system. There is shown a stationary outer plate 61 of an incubator of a automatic culture apparatus while a culture vessel located at a given position within the incubator is shown at 62. A centrifuge tube 63 is located at a position which is higher by "h" in elevation than the vessel 62 and in a vertical plane which is by $\alpha°$ (see FIG. 3) rotated from the latter. A flexible tube 64 may be used to supply a culture solution to the vessel 62 and the tube 63, respectively.

The switching system according to the invention includes a baseplate 65 which is secured to the outer plate 61 of the incubator at a given position. A hollow shaft 66 has a flange 66a, a lower cylindrical portion 66b of a reduced diameter extending downwardly from the flange 66a, and an upper hollow shaft portion 66c of a greater diameter extending upwardly from the flange 66a. The hollow shaft 66 is secured to the baseplate 65 by means of its flange 66a so that the lower cylindrical portion 66b extends through the baseplate 65 and the outer plate 61. A drive shaft 67 is inserted into the lower shaft portion 66b for vertical movement and rotation therein. Intermediate its length, the shaft 67 is peripherally formed with a helical cam groove 67a, and its top portion is formed with a keyway 67b. The shaft 67 has a bulging head 67c having an upper end face which is formed to receive steel ball 68 in a freely rotatable manner. The lower cylindrical portion 66b fixedly carries a pin 69 which engages the cam groove 67a.

A disc-shaped rotating plate 70 includes a short sleeve 70a which is rotatably received between the upper shaft portion 66c and the drive shaft 67. Around its outer periphery, the sleeve 70a is formed with a peripheral groove 70b which is engaged by a pin 71 fixedly carried by the shaft portion 66c. The upper shaft portion 66c fixedly carries a key 72 which engages the keyway 67b, whereby the rotating plate 70 is adapted to rotate integrally with the drive shaft 67, but is prevented from its vertical movement.

A tube support arm 73 extends laterally from the bottom end of the drive shaft 67, and a flexible tube 64 which supplies a culture solution and which is introduced into the incubator from the outside thereof has its free end secured to the free end of the arm 73. A coiled compression spring 74 is disposed between the rotating plate 70 and the head 67c to urge the drive shaft 67 upwardly. A bracket 75 is fixedly mounted on the baseplate 65 and carries a drive motor 76 having an output shaft 76a on which is fixedly mounted an eccentric cam 77, the cam serving to raise and lower the drive shaft 67 through the steel ball 68.

A switch operating member 78 is fixedly mounted on the rotating plate 70. A microswitch or limit switch S10 is fixedly mounted on the baseplate 65 so as to be operated by the member 78 when the discharge port 64a of the tube 64 is located above the vessel 62. Similarly, another microswitch or limit switch S20 is fixedly mounted on the baseplate 65 so as to be operated by the member 78 when the discharge port 64a is located above the centrifuge tube 63, thus forming an angular position detecting mechanism (see FIG. 3).

Figure 4:
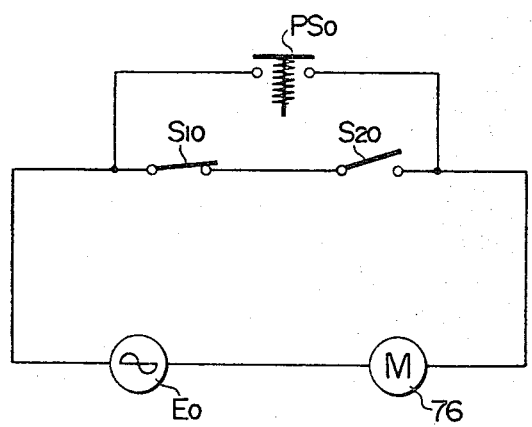
FIG. 4 is a wiring diagram of one exemplary electrical circuit which may be used in the three dimensional switching system shown in FIG. 2.

FIG. 4 shows one exemplary electrical circuit which may be used in the three dimensional switching system mentioned above. The both limit switches S10, S20 which are used to stop the motor form a series circuit together with the drive motor 76 across a power source $E_O$. The series combination of the both limit switches is shunted by a pushbutton switch $PS_O$ which is provided for switching the drive. The switches S1O and S2O are normally closed microswitches and are opened when they are operated by the member 78. It should be understood that the circuit arrangement shown may be modified to enable an automation so that the pushbutton switch $PS_O$ is depressed in connection with the operation of other apparatus or devices contained in the automatic culture apparatus. Alternatively, it may be operated with a timer.

Figure 3:
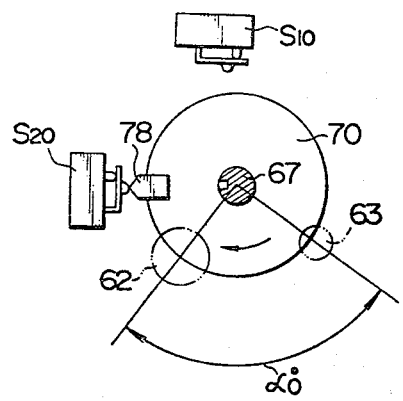
FIG. 3 is a plan view of a rotating plate and an angular position detecting mechanism.

In the condition shown in FIG. 1, the tube 64 which supplies the culture solution has its discharge port 64a located above the centrifuge tube 63, and the operating member 78 is now in engagement with the limit switch S2O to open the circuit (see FIGS. 3 and 4). As a consequence, the motor 76 remains at rest, and the culture solution can be injected into the centrifuge tube 63 during such interval.

Figure 2:
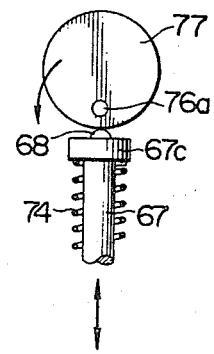
FIG. 2 is a front view of a cam which is used to move a drive shaft up and down.

When the pushbutton switch $PS_O$ is depressed once to close the circuit, the motor 76 is energized, whereby the cam 77 rotates as shown in FIG. 2 to lower the drive shaft 67 against the resilience of the spring 74. As the drive shaft 67 moves down, the engagement between the cam groove 67a and the pin 69 causes the drive shaft 67 to rotate clockwise, as viewed in FIG. 3. The rotation of the drive shaft 67 brings forth an integral rotation of the rotating plate 70 through the engagement between the keyway 67b and the key 72, whereby the operating member 78 moves away from the limit switch S2O to close it. As a result, the motor 76 continues to rotate if the pushbutton switch $PS_O$ is released.

When the discharge port 64a of the tube 64 rotates and moves down to reach position 64aA above the vessel 62, shown in phantom line in FIG. 1, the operating member 78 engages the limit switch S1O to open it, whereby the motor 76 is stopped. The culture solution can then be injected into the vessel 62.

Subsequently when the pushbutton switch $PS_O$ is depressed again, the motor 76 and hence the cam 77 rotate to cause the drive shaft 67 to move upwardly under the influence of the cam 77 and the spring 74, now rotating in the counter-clockwise direction as viewed in FIG. 3. When the discharge port 64a reaches a position above the centrifuge tube 63, the motor is stopped by the action of the limit switch S2O.

In the embodiment described above, the vertical movement of the drive shaft 67 has been controlled by the cam 77, but may be arranged to be achieved by the rotation of the rotating plate 70.

What is claimed is:

1. A liquid supply switching system for automatic culture apparatus comprising a hollow shaft extending through and secured to a stationary outer plate of an incubator, a drive shaft extending through the hollow shaft for rotation and vertical motion therein, the drive shaft being peripherally formed with a keyway and a rotation controlling cam groove in which a pin secured to the hollow shaft is fitted, the drive shaft being urged to move upwardly so that its upper end face bears against a vertical movement controlling cam, a rotating plate carrying a key which engages the keyway and rotatably fitted between the hollow shaft and the drive shaft so as to be capable of only rotation integrally with the drive shaft, a vertical movement controlling cam fixedly mounted on the output shaft of a drive motor and disposed in abutment against the upper end face of the drive shaft for controlling the vertical movement thereof as the motor rotates, a tube support arm extending from the lower end of the drive shaft and adapted to have the inner end of a flexible liquid supply tube mounted thereon, and an angular position detecting mechanism including a switch operating member mounted on the rotating plate and also including a pair of motor stopping limit switches disposed adjacent to the rotating plate at the opposite ends of the angular extent of rotation of the plate, the detecting mechanism causing the switches to deenergize the motor at a given angular position at which the vertical movement of the drive shaft is stopped for bringing the discharge port of the liquid supply tube to a given three dimensional position.

2. A liquid supply switching system according to claim 1 in which the limit switches form a series circuit together with the drive motor, which circuit is connected across a power source, the series combination of the limit switches being shunted by a pushbutton switch which switches the drive.

3. A liquid supply switching system according to claim 1 in which the flexible liquid supply tube is adapted to inject a culture solution into a culture vessel at one of the stop positions and to inject the culture solution into a centrifuge tube at the other stop position.

* * * * *